(12) United States Patent
Jiang et al.

(10) Patent No.: US 12,203,119 B2
(45) Date of Patent: Jan. 21, 2025

(54) METHOD FOR PRODUCING MALTODEXTRIN WITH SINGLE POLYMERIZATION DEGREE BY MULTIENZYME COUPLING

(71) Applicant: Jiangnan University, Wuxi (CN)

(72) Inventors: Bo Jiang, Wuxi (CN); Tao Zhang, Wuxi (CN); Luhua Zheng, Wuxi (CN); Xiaolin Yao, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 728 days.

(21) Appl. No.: 17/340,466

(22) Filed: Jun. 7, 2021

(65) Prior Publication Data

US 2021/0292800 A1    Sep. 23, 2021

Related U.S. Application Data

(63) Continuation of application No. PCT/CN2020/097622, filed on Jun. 23, 2020.

(30) Foreign Application Priority Data

Feb. 24, 2020 (CN) .......................... 202010111929.7

(51) Int. Cl.
*C12P 19/04* (2006.01)

(52) U.S. Cl.
CPC ................... *C12P 19/04* (2013.01)

(58) Field of Classification Search
CPC ....................................... C12P 19/04
See application file for complete search history.

(56) References Cited

FOREIGN PATENT DOCUMENTS

| CN | 108220362 A | 6/2018 | |
|---|---|---|---|
| CN | 108707634 A | 10/2018 | |
| CN | 108866126 A | 11/2018 | |
| CN | 109400760 A | 3/2019 | |
| CN | 110747245 A | * 2/2020 | ........... A23K 20/163 |
| CN | 111304270 A | 6/2020 | |
| WO | 0210427 A1 | 2/2002 | |

OTHER PUBLICATIONS

Ji, et al. Carbohydrate Polymers 210 (2019) 64-7 (Year: 2019).*
Nakada, et al. Biosci. Biotech. Biochem., 59 (12), 221(2210-2214, 1995 (Year: 1995).*
Fang et al. J. Agric. Food Chem., vol. 54, No. 10, 2006 (Year: 2006).*
Varland, et al. Proteomics. Jul. 2015; 15(14): 2385-2401 (Year: 2015).*
Oguma, et al. Appl Microbiol Biotechnol (1993) 39:197-203 (Year: 1993).*
Chaudhuri, et al. J Mol Biol. Jan. 22, 1999;285(3):1179-94 (Year: 1999).*
Burgess-Cassler Current Microbiology vol. 27 (1993), pp. 199-204 (Year: 1993).*

* cited by examiner

*Primary Examiner* — Louise W Humphrey
*Assistant Examiner* — Jessica Faye Edwards
(74) *Attorney, Agent, or Firm* — IPRO, PLLC; Na Xu

(57) ABSTRACT

The disclosure discloses a method for producing maltodextrin with a single polymerization degree by multienzyme coupling, and belongs to the technical field of biology. The disclosure provides a method for producing non-reducing maltodextrin with a uniform and low polymerization degree. After a reaction is preformed for 2-6 hours by using the method of the disclosure, the content of 4-O-α-maltohexaosyl α-D-glucoside in a reaction solution can be as high as 57.2% to 77.3%, accounting for 50% to 90% of the total amount of maltodextrin in the reaction solution. In maltodextrin prepared by using the method of the disclosure, non-reducing maltodextrin with low polymerization degree only includes 4-O-α-maltohexaosyl α-D-glucoside, and the content of non-reducing maltodextrin with low polymerization degree can be 50% to 90% of the total amount of maltodextrin. Therefore, only filtration is needed in preparation of non-reducing maltodextrin with low polymerization degree by using the method of the disclosure; additional separation and purification steps are not needed; high-purity non-reducing maltodextrin with low polymerization degree can be obtained; and the production cost is low.

5 Claims, 2 Drawing Sheets

Specification includes a Sequence Listing.

METHOD FOR PRODUCING MALTODEXTRIN WITH SINGLE POLYMERIZATION DEGREE BY MULTIENZYME COUPLING

TECHNICAL FIELD

The disclosure relates to a method for producing maltodextrin with a single polymerization degree by multienzyme coupling, and belongs to the technical field of biology.

BACKGROUND

Maltodextrin is a product obtained by using starch as a raw material and performing hydrolysis to a low degree according to an acid method or an enzymatic method and has a DE value of 20% or below. Main components of maltodextrin include dextrins with a polymerization degree (namely DP value) of 10 or above and oligosaccharides with a polymerization degree of 10 or below.

Since maltodextrin can be added into foods as a thickener, an emulsifier or a stabilizer and other ingredients, added into medicines as an excipient, a filler and other ingredients and added into daily chemical products as an excellent carrier, maltodextrin has important applications in the fields of food, medicine and daily chemicals, it indicates that maltodextrin has a broad market.

However, due to limitations of existing maltodextrin preparation methods, in currently produced maltodextrin, maltodextrin with high polymerization degree (generally maltodextrin with a DE value of 4% to 12%) contains many linear dextrins and has uneven distribution of DP values, and solutions with addition of such maltodextrin are likely to have precipitates after being placed for a period of time (referring to the following for details: Li Caiming, Li Yang, Gu Zhengbiao, Hong Yan, Cheng Li and Li Zhaofeng, Research Progress on Branching Modification and Characteristics of Maltodextrin [J]. Journal of Chinese Institute of Food Science and Technology. 2018(10):1-8); and maltodextrin with low polymerization degree (generally maltodextrin with a DE value of 13% to 20%) has high reducing ability, easily reacts with other substances and easily undergoes a Maillard reaction with amino acids or proteins, and the quality of products containing this type of maltodextrin is reduced.

In addition, due to limitations of existing maltodextrin preparation methods, currently produced maltodextrin is a mixture of various substances (including glucose, maltose, oligosaccharides, polysaccharides and the like), the difficulty in separating and purifying maltodextrin products with uniform polymerization degrees is greatly increased, and thus the cost of separating and purifying maltodextrin products with uniform polymerization degrees is increased.

Due to the shortcomings above, further development of the maltodextrin market is greatly limited. Therefore, it is urgent to find a low-cost method for producing non-reducing maltodextrin with a uniform and low polymerization degree.

SUMMARY

Technical Problem

A technical problem to be solved by the disclosure is to provide a low-cost method for producing non-reducing maltodextrin with a uniform and low polymerization degree.

Technical Solutions

In order to solve the technical problem above, the disclosure provides a method for producing maltodextrin, and the maltodextrin is non-reducing maltodextrin. The method includes: first adding a cyclodextrin degrading enzyme (CDase) and a maltooligosyltrehalose synthase (MTSase) into cyclodextrin for reaction to obtain a reaction solution containing maltodextrin, and then obtaining maltodextrin from the reaction solution containing maltodextrin.

In an embodiment of the disclosure, the amino acid sequence of the cyclodextrin degrading enzyme is set forth as SEQ ID NO:2.

In an embodiment of the disclosure, the amino acid sequence of the maltooligosyltrehalose synthase is set forth as SEQ ID NO:3.

In an embodiment of the disclosure, the nucleotide sequence of a gene encoding a cyclodextrin glucosyltransferase is set forth as SEQ ID NO:4.

In an embodiment of the disclosure, the nucleotide sequence of a gene encoding the cyclodextrin degrading enzyme is set forth as SEQ ID NO:5.

In an embodiment of the disclosure, the nucleotide sequence of a gene encoding the maltooligosyltrehalose synthase is set forth as SEQ ID NO:6.

In an embodiment of the disclosure, the addition amount of the cyclodextrin degrading enzyme in the cyclodextrin solution is 0.5-5 $U/g_{cyclodextrin}$; and the addition amount of the maltooligosyltrehalose synthase in the cyclodextrin solution is 10-100 $U/g_{cyclodextrin}$.

In an embodiment of the disclosure, the reaction temperature is 25-65° C., and the pH is 5.0-8.5.

In an embodiment of the disclosure, the cyclodextrin is α-cyclodextrin, β-cyclodextrin and/or γ-cyclodextrin.

In an embodiment of the disclosure, the non-reducing maltodextrin is 4-O-α-maltopentaosyl α-D-glucoside, 4-O-α-maltohexaosyl α-D-glucoside and/or 4-O-α-maltoheptosyl α-D-glucoside.

In an embodiment of the disclosure, the non-reducing maltodextrin is 4-O-α-maltohexaosyl α-D-glucoside.

In an embodiment of the disclosure, the cyclodextrin degrading enzyme and the maltooligosyltrehalose synthase are added into the cyclodextrin for reaction for 4 hours.

The disclosure also provides maltodextrin prepared by using the method.

The disclosure also provides application of the method in preparation of maltodextrin, foods containing maltodextrin, medicines containing maltodextrin or daily chemical products containing maltodextrin.

The disclosure also provides application of the cyclodextrin degrading enzyme and/or the maltooligosyltrehalose synthase in production of non-reducing maltodextrin. The non-reducing maltodextrin is 4-O-α-maltopentaosyl α-D-glucoside, 4-O-α-maltohexaosyl α-D-glucoside and/or 4-O-α-maltoheptosyl α-D-glucoside.

The amino acid sequence of the cyclodextrin degrading enzyme may be selected as set forth as SEQ ID NO:2.

The amino acid sequence of the maltooligosyltrehalose synthase may be selected as set forth as SEQ ID NO:3.

In an embodiment of the disclosure, the nucleotide sequence of a gene encoding the cyclodextrin degrading enzyme is set forth as SEQ ID NO:5.

In an embodiment of the disclosure, the nucleotide sequence of a gene encoding the maltooligosyltrehalose synthase is set forth as SEQ ID NO:6.

Beneficial Effects (1) The disclosure provides a method for producing non-reducing maltodextrin with a uniform and low polymerization degree. After a reaction is preformed for 2-6 hours by using the method of the disclosure, the content of 4-O-α-maltohexaosyl α-D-glucoside in a reaction solution can be as high as 57.2% to 77.3%, accounting for 50% to 90% of the total amount of maltodextrin in the reaction solution.

(2) In maltodextrin prepared by using the method of the disclosure, non-reducing maltodextrin with low polymerization degree only includes 4-O-α-maltohexaosyl α-D-glucoside; and in the maltodextrin prepared by using the method of the disclosure, the content of non-reducing maltodextrin with low polymerization degree can be 50% to 90% of the total amount of maltodextrin. Therefore, only filtration is needed in preparation of non-reducing maltodextrin with low polymerization degree by using the method of the disclosure; additional separation and purification steps are not needed; high-purity non-reducing maltodextrin with low polymerization degree can be obtained; and the production cost is low.

DETAILED DESCRIPTION

Figure 1:
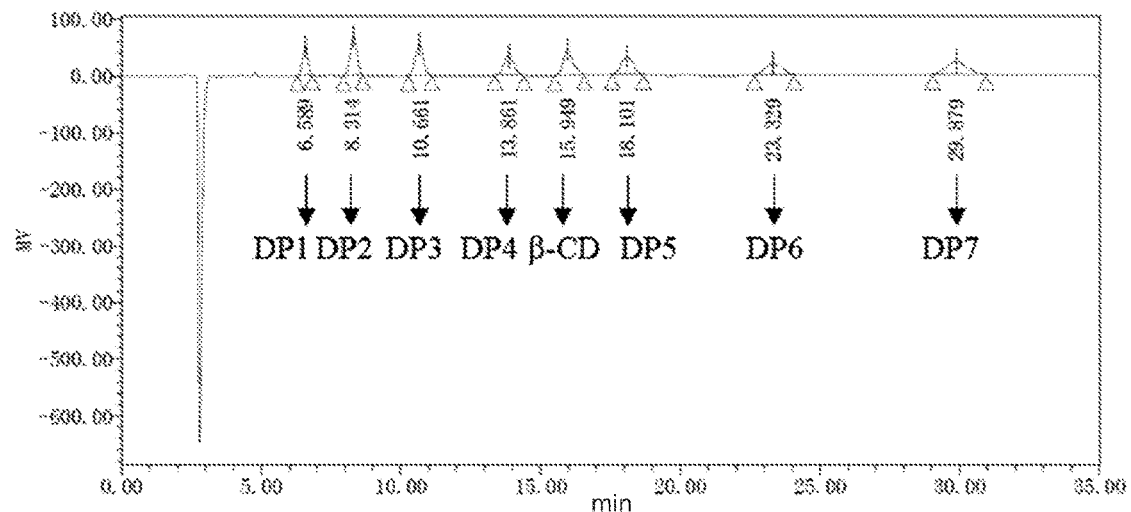
FIG. 1: A liquid phase distribution diagram of standard products (70% acetonitrile concentration).

*Escherichia coli* DH5a and *E. coli* BL21 (DE3) involved in the following examples are purchased from General Biotechnology Co., Ltd.; a pET-28a(+) vector involved in the following examples is purchased from Invitrogen; corn starch involved in the following examples is purchased from Shanghai Aladdin Co., Ltd.; and β-cyclodextrin involved in the following examples is purchased from Shanghai Sangon Co., Ltd.

Culture Media Involved in the Following Examples are as Follows:

LB liquid culture medium: 10 g/L of tryptone, 5 g/L of a yeast extract and 10 g/L of sodium chloride, and 100 μg/mL of kanamycin is added before use.

LB solid culture medium: 10 g/L of tryptone, 5 g/L of a yeast extract, 10 g/L of sodium chloride and 15 g/L of agar, and 100 μg/mL of kanamycin is added before use.

Preparation Methods Involved in the Following Examples are as Follows:

A Preparation Method of Cyclodextrin Glucosyltransferase (CGTase) is as Follows:

A gene (the nucleotide sequence is set forth as SEQ ID NO:4) encoding a cyclodextrin glucosyltransferase with the amino acid sequence set forth as SEQ ID NO:1 is synthesized; restriction endonucleases Hind III and Nde I are used to perform digestion on the obtained gene and a pET-28a(+) vector, and two obtained digested products are ligated with T4 ligase to obtain a ligated product; the obtained ligated product is placed overnight at 16° C. for 15 hours and then transformed into *E. coli* DH5a competent cells; the transformed *E. coli* DH5a competent cells are spread on an LB solid culture medium (containing 10 μg/mL of kanamycin) and inverted for culture at 37° C. for 24 hours; positive transformants are picked, a plasmid is extracted, it is shown through sequencing verification results that ligation is successful, and a recombinant plasmid pET-28a(+)-CGTase is obtained; the obtained recombinant plasmid pET-28a(+)-CGTase is introduced into *E. coli* BL21(DE3) to obtain recombinant *E. coli* BL21(DE3)/pET-28a(+)-CGTase; the obtained recombinant *E. coli* BL21(DE3)/pET-28a(+)-CGTase is streaked on the LB solid culture medium and cultured in a constant-temperature incubator at 37° C. for 18 hours to obtain single colonies; the single colonies are picked, respectively inoculated into an LB liquid culture medium, cultured in a shaker at 37° C. and 200 rpm for 14 hours and continuously activated for 3 generations to obtain activated bacteria solutions; the activated bacteria solutions are respectively inoculated into the LB liquid culture medium according to an inoculation amount of 1% (v/v) for culture at the temperature of 37° C. and a rotation speed of 200 rpm for 12 hours to obtain a fermentation solution; and the fermentation solution is centrifuged to obtain a fermentation supernatant, namely a crude enzyme solution, named as CGTase, of the cyclodextrin glucosyltransferase with the amino acid sequence set forth as SEQ ID NO:1.

A Preparation Method of Cyclodextrin Degrading Enzyme (CDase) is as Follows:

A gene (the nucleotide sequence is set forth as SEQ ID NO:5) encoding a cyclodextrin degrading enzyme with the amino acid sequence set forth as SEQ ID NO:2 is synthesized; and a crude enzyme solution, named as CDase, of the cyclodextrin degrading enzyme with the amino acid sequence set forth as SEQ ID NO:2 is prepared by taking the method for preparing CGTase as a reference.

A Preparation Method of Maltooligosyltrehalose Synthase (MTSase) is as Follows:

A gene (the nucleotide sequence is set forth as SEQ ID NO:6) encoding a maltooligosyltrehalose synthase with the amino acid sequence set forth as SEQ ID NO:3 is synthesized; and a crude enzyme solution, named as MTSase, of the maltooligosyltrehalose synthase with the amino acid sequence set forth as SEQ ID NO:3 is prepared by taking the method for preparing CGTase as a reference.

A Preparation Method of a Gelatinized Starch Solution is as Follows:

Corn starch is added into a sodium phosphate buffer with the concentration of 20 mM to obtain a corn starch solution with the corn starch concentration of 30 g/L; and the corn starch solution is stirred in a boiling water bath at a speed of 150 r/min for 30 minutes to obtain the gelatinized starch solution.

A Preparation Method of a Cyclodextrin Solution is as Follows:

β-cyclodextrin is added into a sodium phosphate buffer with the concentration of 20 mM to obtain a cyclodextrin solution with the β-cyclodextrin concentration of 20 g/L.

Detection Methods Involved in the Following Examples are as Follows:

A Method for Detecting the Content of Glucose, Maltose, Maltotriose, Maltotetraose, Maltopentaose, Maltohexaose, Maltoheptaose, α-Cyclodextrin, β-Cyclodextrin or γ-Cyclodextrin in a Reaction Solution:

A high performance liquid chromatography (HPLC) method is used;

Chromatographic column: an amino column (Shodex NH2P-50 4E);

Mobile phase: acetonitrile:water=60% to 70% (v/v);

Standard products: 0.5 g of standard product of each of glucose (DP1), maltose (DP2), maltotriose (DP3), maltotetraose (DP4), maltopentaose (DP5), maltohexaose (DP6), maltoheptaose (DP7), α-cyclodextrin (α-CD), β-cyclodextrin (β-CD) or γ-cyclodextrin (γ-CD) (with the purity of 99.5%) is weighed with a precision of 0.0001 g; the standard products are dissolved in ultrapure water to 50 mL, uniformly shaken and filtered with a 0.22 μm microporous membrane; and a filtrate is collected for determination (liquid phase distribution of the standard products is shown in FIG. 1);

Sample preparation: a reaction solution obtained after reaction is centrifuged at 12000 r/min for 10 minutes and filtered with a 0.22 μm microporous membrane, and a filtrate is collected for determination;

Sample measurement: a pipe is flushed with the mobile phase at a flow rate of 1 mL/min for 30 minutes at first; the chromatographic column is installed; the mobile phase used is introduced into a reference cell for 60 minutes before formal sample introduction and analysis; a baseline is placed stably, and then 10 μL of a standard solution and 10 μL of the prepared sample are respectively introduced; sugar components in the sample are qualitatively determined according to the retention time of the standard products, and the ratio of the sugar components is calculated by using an internal standard method according to a peak area of the sample.

A Method for Detecting the Cyclodextrin Glucosyltransferase Activity:

10 μL of CGTase is added into 250 μL of a gelatinized starch solution with the concentration of 30 g/L, and then the solution is supplemented to 500 μL with a 20 mM phosphate buffer to obtain a reaction system; the reaction system is subjected to a reaction at the temperature of 55° C. and the pH of 7.0 for 10 minutes and then boiled to kill enzymes, the production amount of cyclodextrin is detected by using a liquid chromatography method, and the cyclodextrin glucosyltransferase activity of CGTase is obtained.

The cyclodextrin glucosyltransferase activity is defined as follows: the amount of enzyme required to produce 1 μmol cyclodextrin by acting on gelatinized starch within 1 minute at the temperature of 55° C. and the pH of 7.0 is one enzyme activity unit (1 U).

A Method for Detecting the Cyclodextrin Degrading Enzyme Activity:

10 μL of CDase is added into 250 μL of a β-cyclodextrin solution with the concentration of 20 g/L, and then the solution is supplemented to 500 μL with a 20 mM phosphate buffer to obtain a reaction system; the reaction system is subjected to a reaction at the temperature of 35° C. and the pH of 7.5 for 30 minutes and then boiled to kill enzymes, the production amount of maltoheptaose is detected by using a liquid chromatography method, and the cyclodextrin glucosyltransferase activity of CDase is obtained.

The cyclodextrin degrading enzyme activity is defined as follows: the amount of enzyme required to produce 1 μmol maltoheptaose by acting on β-cyclodextrin within 1 minute at the temperature of 35° C. and the pH of 7.5 is one enzyme activity unit (1 U).

A Method for Detecting the Maltooligosyltrehalose Synthase Activity:

5 μL of MTSase is added into 250 μL of a maltodextrin solution with the concentration of 20 g/L, and then the solution is supplemented to 500 μL with a 20 mM phosphate buffer to obtain a reaction system; the reaction system is subjected to a reaction at the temperature of 45° C. and the pH of 7.0 for 10 minutes and then boiled to kill enzymes, the decrease amount of the reducing ability of a reaction solution is detected by using a DNS method, and the maltooligosyltrehalose synthase activity of MTSase is obtained.

The maltooligosyltrehalose synthase activity is defined as follows: the amount of enzyme required to produce 1 μmol α-1,4-glycosidic bond by acting on maltodextrin within 1 minute at the temperature of 45° C. and the pH of 7.0 is one enzyme activity unit (1 U).

A Method for Detecting the DE Value (Reducing Value) of a Reaction Solution (DNS Colorimetric Method):

Referring to the following for details: Yan Fanhe, Zhou Jinmei, Wu Ruchun. Determination of Content of Reducing Sugars in Bagasse by Using DNS Method [J]. Food Research and Development. 36(02): 126-128.

The DE value (reducing value) is defined as follows: a ratio of the amount of reducing sugars to the total amount of solids in a system.

Example 1: Preparation of Maltodextrin (Single Enzyme)

Specific steps are as follows:

Solution 1: CGTase was added into a gelatinized starch solution at the addition amount of 7 $U/g_{starch}$ for an enzymatic reaction at the temperature of 55° C. and the pH of 7.0 for 3 hours to obtain a reaction solution 1.

Solution 2: CDase was added into a gelatinized starch solution at the addition amount of 5 $U/g_{starch}$ for an enzymatic reaction at the temperature of 35° C. and the pH of 7.5 for 4 hours to obtain a reaction solution 2.

Solution 3: MTSase was added into a gelatinized starch solution at the addition amount of 45 $U/g_{starch}$ for an enzymatic reaction at the temperature of 45° C. and the pH of 7.0 for 4 hours to obtain an enzymatic reaction 3.

Solution 4: CDase was added into a β-cyclodextrin solution at the addition amount of 1.5 $U/g_{cyclodextrin}$ for an enzymatic reaction at the temperature of 35° C. and the pH of 7.5 for 4 hours to obtain a reaction solution 4.

Solution 5: MTSase was added into a β-cyclodextrin solution at the addition amount of 15 $U/g_{cyclodextrin}$ for an enzymatic reaction at the temperature of 45° C. and the pH of 7.0 for 4 hours to obtain an enzymatic reaction 5.

Figure 2:
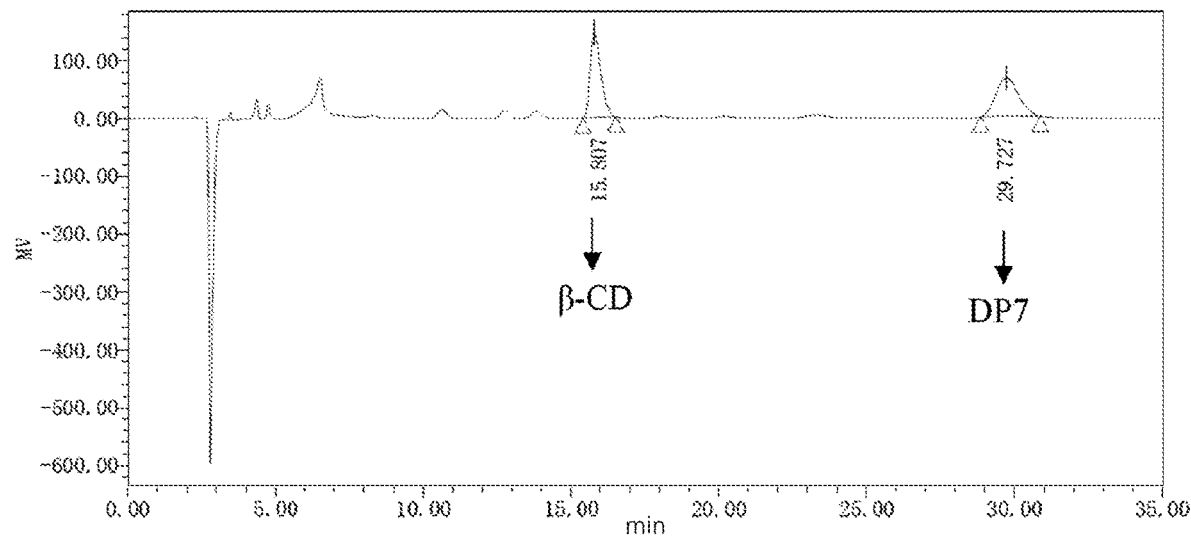
FIG. 2: A liquid phase distribution diagram of products in reaction solution 4 (70% acetonitrile concentration).

Polymerization degree distribution of maltodextrin in the reaction solutions 1 to 5 was detected, and non-reducing maltoheptaose (namely 4-O-α-maltoheptosyl α-D-glucoside) was represented by NDP7 (polymerization degree distribution of maltodextrin in the reaction solutions 1 to 5 is shown in Table 1, and liquid phase distribution of products in the reaction solution 4 is shown in FIG. 2).

It can be seen from Table 1 that CGTase, CDase and MTSase cannot act on starch alone to produce non-reducing maltodextrin with a uniform and low polymerization degree, and CDase and MTSase cannot act on cyclodextrin alone to produce non-reducing maltodextrin with a uniform and low polymerization degree; and reducing maltodextrin with low polymerization degree in the reaction solution obtained by CDase reaction has the highest content and the most uniform polymerization degree.

TABLE 1

Polymerization degree distribution of maltodextrin in the reaction solutions 1 to 5

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 1 | 7.0 | 75.0 | 18.0 | / | / | / | / | / | / | / | / |
| Reaction solution 2 | / | / | / | / | / | / | / | / | / | / | / |
| Reaction solution 3 | / | / | / | / | / | / | / | / | / | / | / |
| Reaction solution 4 | / | 45.4 | / | / | 3.5 | 2.6 | 3.6 | / | / | 44.9 | / |
| Reaction solution 5 | / | / | / | / | / | / | / | / | / | / | / |

Note:
"/" means undetectable

Example 2: Preparation of Maltodextrin (Enzyme Coupling and a One-Step Method)

Specific steps are as follows:

Solution 1: CGTase and CDase were added into a gelatinized starch solution at the addition amount of 7 g U/$g_{starch}$ and 5 g U/$g_{starch}$ respectively for an enzymatic reaction at the temperature of 40° C. and the pH of 7.0 for 4 hours to obtain a reaction solution 6.

Solution 2: CDase and MTSase were added into a β-cyclodextrin solution at the addition amount of 1.5 U/$g_{cyclodextrin}$ and 15 U/$g_{cyclodextrin}$ respectively for an enzymatic reaction at the temperature of 40° C. and the pH of 7.0 for 4 hours to obtain a reaction solution 7.

Solution 3: CGTase, CDase and MTSase were added into a gelatinized starch solution at the addition amount of 7 U/$g_{starch}$, 5 U/$g_{starch}$ and 45 g U/$g_{starch}$ respectively for an enzymatic reaction at the temperature of 40° C. and the pH of 7.0 for 4 hours to obtain a reaction solution 8.

Polymerization degree distribution of maltodextrin in the reaction solutions 6 to 8 was detected (polymerization degree distribution of maltodextrin in the reaction solutions 6 to 8 is shown in Table 2).

It can be seen from Table 2 that MTSase is the key to producing non-reducing maltodextrin with low polymerization degree, and non-reducing maltodextrin with low polymerization degree cannot be produced without MTSase; in addition, it can be seen from Table 2 that non-reducing maltodextrin with low polymerization degree produced by using cyclodextrin as a substrate and using CDase and MTSase according to a one-step method has high yield and high uniformity.

TABLE 2

Polymerization degree distribution of maltodextrin in the reaction solutions 6 to 8

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 6 | 8.7 | 32.7 | 14.1 | / | 13.6 | 11.8 | / | / | / | 19.1 | / |
| Reaction solution 7 | / | 6.1 | / | / | 4.1 | 5.9 | 6.6 | / | / | / | 77.3 |
| Reaction solution 8 | 17.7 | 17.8 | 5.9 | / | 16 | 24.7 | / | / | / | 11.8 | 6.1 |

Note:
"/" means undetectable

Example 3: Preparation of Maltodextrin (Enzyme Coupling and a Fractional-Step Method)

Specific steps are as follows:

Solution 1: First, CGTase was added into a gelatinized starch solution at the addition amount of 7 U/$g_{starch}$ for an enzymatic reaction at the temperature of 55° C. and the pH of 7.0 for 3 hours, and then CDase was added into the gelatinized starch solution at the addition amount of 5 U/$g_{starch}$ for an enzymatic reaction at the temperature of 35° C. and the pH of 7.5 for 4 hours to obtain a reaction solution 9.

Solution 2: First, CGTase was added into a gelatinized starch solution at the addition amount of 7 U/$g_{starch}$ for an enzymatic reaction at the temperature of 55° C. and the pH of 7.0 for 3 hours, then CDase was added into the gelatinized starch solution at the addition amount of 5 U/$g_{starch}$ for an enzymatic reaction at the temperature of 35° C. and the pH of 7.5 for 4 hours, and finally MTSase was added into the gelatinized starch solution at the addition amount of 45 U/g$_{starch}$ for an enzymatic reaction at the temperature of 45° C. and the pH of 7.0 for 4 hours to obtain a reaction solution 10.

Solution 3: First, CDase was added into a β-cyclodextrin solution at the addition amount of 1.5 U/g$_{cyclodextrin}$ for an enzymatic reaction at the temperature of 35° C. and the pH of 7.5 for 4 hours, and then MTSase was added into the β-cyclodextrin solution at the addition amount of 15 U/g$_{cyclodextrin}$ for an enzymatic reaction at the temperature of 45° C. and the pH of 7.0 for 4 hours to obtain a reaction solution 11.

Figure 3:
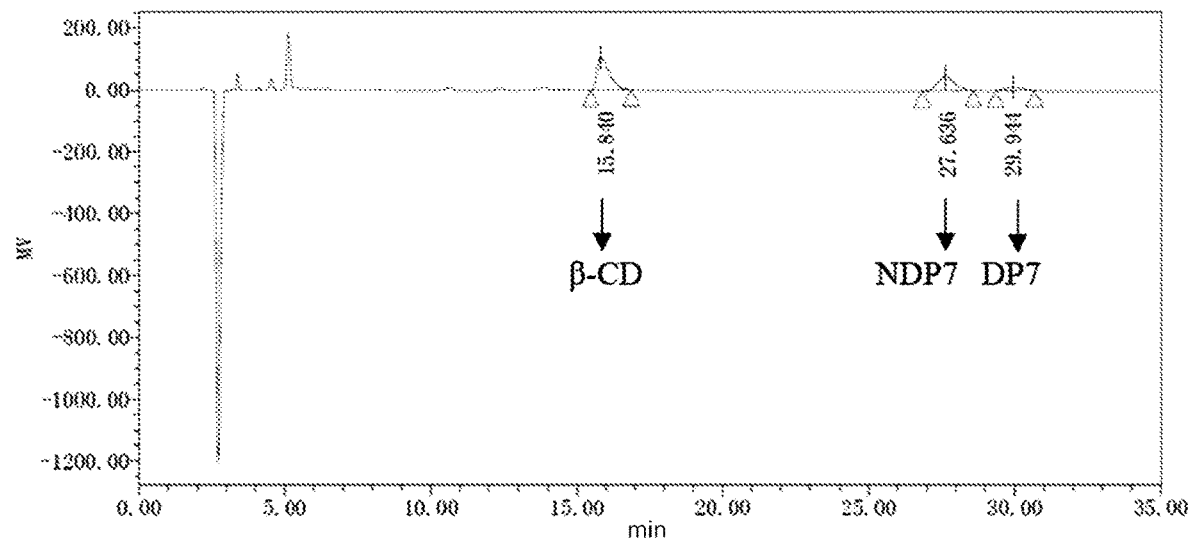
FIG. 3: A liquid phase distribution diagram of products in reaction solution 11 (70% acetonitrile concentration).

Polymerization degree distribution of maltodextrin in the reaction solutions 9 to 11 was detected (polymerization degree distribution of maltodextrin in the reaction solutions 9 to 11 is shown in Table 3, and liquid phase distribution of products in the reaction solution 11 is shown in FIG. 3).

It can be seen from Table 3 that MTSase is the key to producing non-reducing maltodextrin with low polymerization degree, and non-reducing maltodextrin with low polymerization degree cannot be produced without MTSase; in addition, it can be seen from Table 3 that the yield and uniformity of non-reducing maltodextrin with low polymerization degree produced by using a fractional-step method are far lower than those of Solution 2 (one-step method) in Example 2.

When starch is used as the substrate, maltodextrin with a single polymerization degree can be produced only when two or three enzymes are reacted in series.

TABLE 3

Polymerization degree distribution of maltodextrin in the reaction solutions 9 to 11

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 9 | 9.8 | 38.1 | 14.2 | / | 12.8 | 9.5 | / | / | / | 15.6 | / |
| Reaction solution 10 | 14.2 | 2.9 | 10.5 | / | 20.2 | 35.4 | / | / | / | 3.8 | 13 |
| Reaction solution 11 | / | 42.5 | / | / | 3.9 | 3.0 | 3.9 | / | / | 7.5 | 39.2 |

Note:
"/" means undetectable

Example 4: The Effect of Enzyme Addition Amount on the Yield of Maltodextrin On the basis of Solution 2 in Example 2, the addition amount of CDase was changed into 0.5 U/g$_{cyclodextrin}$, 1.5 U/g$_{cyclodextrin}$, 2.5 U/g$_{cyclodextrin}$, 3.5 U/g$_{cyclodextrin}$ and 4.5 U/g$_{cyclodextrin}$ to obtain reaction solutions 12 to 16 respectively.

Figure 4:
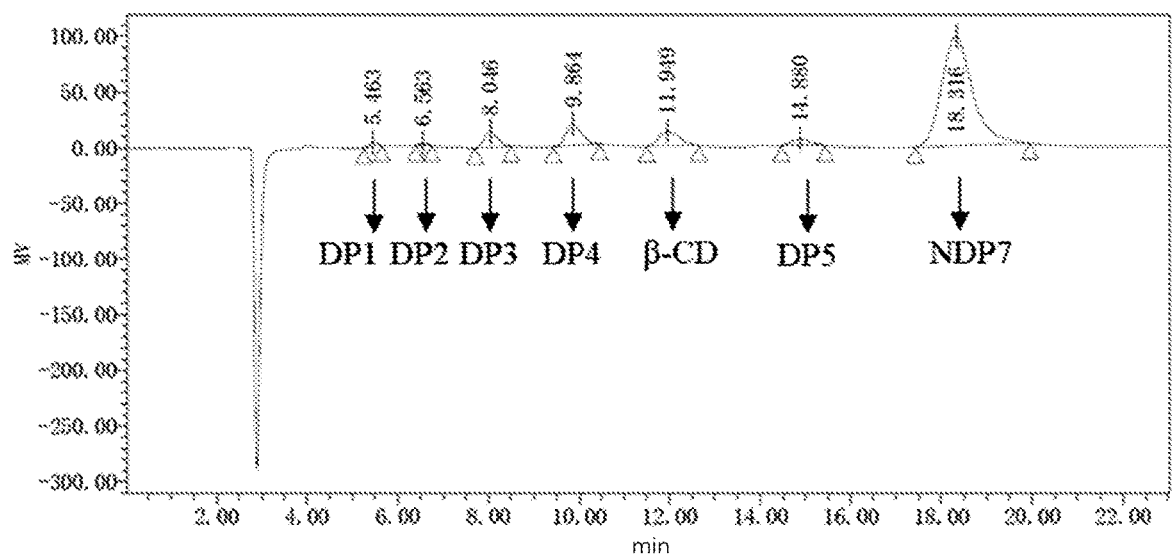
FIG. 4: A liquid phase distribution diagram of products in reaction solution 13 (65% acetonitrile concentration).

Polymerization degree distribution of maltodextrin in the reaction solutions 12 to 16 was detected (detection results are shown in Table 4, and liquid phase distribution of products in the reaction solution 13 is shown in FIG. 4).

It can be seen from Table 4 that when the addition amount of CDase is 1.5 U/g$_{cyclodextrin}$, non-reducing maltodextrin with low polymerization in the reaction solution has the highest content and the most uniform polymerization degree.

TABLE 4

Polymerization degree distribution of maltodextrin in the reaction solutions 12 to 16

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 12 | / | 66.2 | / | / | 2.5 | / | / | / | / | / | 31.3 |
| Reaction solution 13 | / | 6.1 | / | / | 4.1 | 5.9 | 6.6 | / | / | / | 77.3 |
| Reaction solution 14 | / | / | / | / | 6.4 | 17.1 | 13.4 | / | / | / | 63.1 |

TABLE 4-continued

Polymerization degree distribution of maltodextrin in the reaction solutions 12 to 16

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 15 | / | / | / | / | 7.8 | 21.9 | 17.2 | 4.0 | 4.9 | / | 44.2 |
| Reaction solution 16 | / | / | / | 2.5 | 13.3 | 30.6 | 17.3 | 2.7 | 4.3 | / | 29.3 |

Note:
"/" means undetectable

Example 5: The Effect of Enzymatic Reaction Time on the Yield of Maltodextrin On the basis of Solution 2 in Example 2, the reaction time was changed into 30 minutes, 1 hour, 2 hours, 4 hours and 6 hours to obtain reaction solutions 17 to 21 respectively.

Polymerization degree distribution of maltodextrin in the reaction solutions 17 to 21 was detected (detection results are shown in Table 5).

It can be seen from Table 5 that when the reaction is performed for 4 hours, non-reducing maltodextrin with low polymerization in the reaction solution has the highest content and the most uniform polymerization degree.

TABLE 5

Polymerization degree distribution of maltodextrin in the reaction solutions 17 to 21

| | α-cyclodextrin (%) | β-cyclodextrin (%) | γ-cyclodextrin (%) | DP 1 (%) | DP 2 (%) | DP 3 (%) | DP 4 (%) | DP 5 (%) | DP 6 (%) | DP 7 (%) | NDP 7 (%) |
|---|---|---|---|---|---|---|---|---|---|---|---|
| Reaction solution 17 | / | 100 | / | / | | | | / | / | / | / |
| Reaction solution 18 | / | 74.7 | / | / | 3.2 | | | / | / | | 22.1 |
| Reaction solution 19 | / | 40.0 | / | / | 1.4 | 0.8 | 0.6 | / | / | | 57.2 |
| Reaction solution 20 | / | 6.1 | / | | 4.1 | 5.9 | 6.6 | | | | 77.3 |
| Reaction solution 21 | / | | / | 0.7 | 7.2 | 13.3 | 11.1 | 3.1 | 3.8 | | 60.8 |

Note:
"/" means undetectable

Example 6: Determination of the DE Value of Non-Reducing Maltoheptaose

The reaction solution 7 in Example 2 was taken and subjected to semi-preparative liquid chromatography to obtain NDP7 with the purity of 92% (v/v); the DE value of NDP7 was measured by using a DNS colorimetric method; and a measurement result is shown in Table 6. It can be seen from Table 6 that the DE value of NDP7 is as low as only 3%, it indicates that NDP7 is a non-reducing sugar.

TABLE 6

Determination of the DE value of NDP7

| Sugar preparation | Purity (%) | DE value (%) |
|---|---|---|
| NDP7 | 92 | 3 |

Although the disclosure has been disclosed as above in preferred examples, the examples are not intended to limit the disclosure. Various changes and modifications can be made by anyone familiar with this technology without departing from the spirit and scope of the disclosure. Therefore, the protection scope of the disclosure should be defined by the claims.

What is claimed is:

1. A method for producing maltodextrin, comprising:
adding cyclodextrin into water or a buffer to obtain a cyclodextrin solution; and
adding a cyclodextrin degrading enzyme with the amino acid sequence of SEQ ID NO: 2 and a maltooligosyltrehalose synthase together in a one-step reaction to the cyclodextrin solution thereby obtaining maltodextrin, wherein:
the maltodextrin is 4-O-α-maltoheptosyl α-D-glucoside,
the cyclodextrin degrading enzyme added to the cyclodextrin solution is 0.5 $U/g_{cyclodextrin}$ to 5 $U/g_{cyclodextrin}$,
the maltooligosyltrehalose synthase added to the cyclodextrin solution is 10 $U/g_{cyclodextrin}$ to 100 $U/g_{cyclodextrin}$,
the reaction temperature is 25° C. to 65° C., and
the cyclodextrin solution has a pH value of 5.0 to 8.5.

2. The method according to claim 1, wherein the amino acid sequence of the maltooligosyltrehalose synthase is set forth as SEQ ID NO:3.

3. The method according to claim 1, wherein the cyclodextrin degrading enzyme and the maltooligosyltrehalose synthase are incubated with the cyclodextrin solution for reaction for 4 hours.

4. The method according to claim 1, wherein the cyclodextrin comprises one or more of a-cyclodextrin, β-cyclodextrin, and γ-cyclodextrin.

5. The method according to claim 1, wherein purity of the maltodextrin after completion of the method is 92% or greater with a DE value of 3% or less, wherein the DE value is defined as a ratio of an amount of reducing sugars to a total amount of solids.

* * * * *

SEQUENCE LISTING

<160> NUMBER OF SEQ ID NOS: 6

<210> SEQ ID NO 1
<211> LENGTH: 682
<212> TYPE: PRT
<213> ORGANISM: Artificial Sequence
<220> FEATURE:
<223> OTHER INFORMATION: Translated from Synthetic DNA

<400> SEQUENCE: 1

Met Lys Arg Phe Met Lys Leu Thr Ala Val Trp Thr Leu Trp Leu Ser
1               5                   10                  15

Leu Thr Leu Gly Leu Leu Ser Pro Val His Ala Ala Pro Asp Thr Ser
            20                  25                  30

Val Ser Asn Lys Gln Asn Phe Ser Thr Asp Val Ile Tyr Gln Ile Phe
        35                  40                  45

Thr Asp Arg Phe Ser Asp Gly Asn Pro Ala Asn Asn Pro Thr Gly Ala
    50                  55                  60

Ala Phe Asp Gly Ser Cys Thr Asn Leu Arg Leu Tyr Cys Gly Gly Asp
65                  70                  75                  80

Trp Gln Gly Ile Ile Asn Lys Ile Asn Asp Gly Tyr Leu Thr Gly Met
                85                  90                  95

Gly Ile Thr Ala Ile Trp Ile Ser Gln Pro Val Glu Asn Ile Tyr Ser
            100                 105                 110

Val Ile Asn Tyr Ser Gly Val His Asn Thr Ala Tyr His Gly Tyr Trp
        115                 120                 125

Ala Arg Asp Phe Lys Lys Thr Asn Pro Ala Tyr Gly Thr Met Gln Asp
    130                 135                 140

Phe Lys Asn Leu Ile Asp Thr Ala His Ala His Asn Ile Lys Val Ile
145                 150                 155                 160

Ile Asp Phe Ala Pro Asn His Thr Ser Pro Ala Ser Ser Asp Asp Pro
                165                 170                 175

Ser Phe Ala Glu Asn Gly Arg Leu Tyr Asp Asn Gly Asn Leu Leu Gly
            180                 185                 190

Gly Tyr Thr Asn Asp Thr Gln Asn Leu Phe His Tyr Gly Gly Thr
        195                 200                 205

Asp Phe Ser Thr Ile Glu Asn Gly Ile Tyr Lys Asn Leu Tyr Asp Leu
    210                 215                 220

Ala Asp Leu Asn His Asn Asn Ser Ser Val Asp Val Tyr Leu Lys Asp
225                 230                 235                 240

Ala Ile Lys Met Trp Leu Asp Leu Gly Val Asp Gly Ile Arg Val Asp
                245                 250                 255

Ala Val Lys His Met Pro Phe Gly Trp Gln Lys Ser Phe Met Ser Thr
            260                 265                 270

Ile Asn Asn Tyr Lys Pro Val Phe Thr Phe Gly Glu Trp Phe Leu Gly
        275                 280                 285

Ile Asn Glu Ile Ser Pro Glu Tyr His Gln Phe Ala Asn Glu Ser Gly
    290                 295                 300

Met Ser Leu Leu Asp Phe Arg Phe Ala Gln Lys Ala Arg Gln Val Phe
305                 310                 315                 320

Arg Asp Asn Thr Asp Asn Met Tyr Gly Leu Lys Ala Met Leu Glu Gly
                325                 330                 335

Ser Glu Val Asp Tyr Ala Gln Val Asn Asp Gln Val Thr Phe Ile Asp
            340                 345                 350

```
Asn His Asp Met Glu Arg Phe His Thr Ser Asn Gly Asp Arg Arg Lys
        355                 360                 365

Leu Glu Gln Ala Leu Ala Phe Thr Leu Thr Ser Arg Gly Val Pro Ala
370                 375                 380

Ile Tyr Tyr Gly Ser Glu Gln Tyr Met Ser Gly Gly Asn Asp Pro Asp
385                 390                 395                 400

Asn Arg Ala Arg Ile Pro Ser Phe Ser Thr Thr Thr Ala Tyr Gln
                405                 410                 415

Val Ile Gln Lys Leu Ala Pro Leu Arg Lys Ser Asn Pro Ala Ile Ala
                420                 425                 430

Tyr Gly Ser Thr Gln Glu Arg Trp Ile Asn Asn Asp Val Ile Ile Tyr
                435                 440                 445

Glu Arg Lys Phe Gly Asn Asn Val Ala Val Ala Ile Asn Arg Asn
    450                 455                 460

Met Asn Thr Pro Ala Ser Ile Thr Gly Leu Val Thr Ser Leu Pro Gln
465                 470                 475                 480

Gly Ser Tyr Asn Asp Val Leu Gly Gly Ile Leu Asn Gly Asn Thr Leu
                485                 490                 495

Thr Val Gly Ala Gly Gly Ala Ala Ser Asn Phe Thr Leu Ala Pro Gly
                500                 505                 510

Gly Thr Ala Val Trp Gln Tyr Thr Thr Asp Ala Thr Ala Pro Ile Ile
                515                 520                 525

Gly Asn Val Gly Pro Met Met Ala Lys Pro Gly Val Thr Ile Thr Ile
                530                 535                 540

Asp Gly Arg Gly Phe Gly Ser Gly Lys Gly Thr Val Tyr Phe Gly Thr
545                 550                 555                 560

Thr Ala Val Thr Gly Ala Asp Ile Val Ala Trp Glu Asp Thr Gln Ile
                565                 570                 575

Gln Val Lys Ile Pro Ala Val Pro Gly Gly Ile Tyr Asp Ile Arg Val
                580                 585                 590

Ala Asn Ala Ala Gly Ala Ala Ser Asn Ile Tyr Asp Asn Phe Glu Val
                595                 600                 605

Leu Thr Gly Asp Gln Val Thr Val Arg Phe Val Ile Asn Asn Ala Thr
        610                 615                 620

Thr Ala Leu Gly Gln Asn Val Phe Leu Thr Gly Asn Val Ser Glu Leu
625                 630                 635                 640

Gly Asn Trp Asp Pro Asn Asn Ala Ile Gly Pro Met Tyr Asn Gln Val
                645                 650                 655

Val Tyr Gln Tyr Pro Thr Trp Tyr Tyr Asp Val Ser Val Pro Ala Gly
                660                 665                 670

Gln Thr Ile Glu Phe Lys Phe Leu Lys Lys
                675                 680

<210> SEQ ID NO 2
<211> LENGTH: 592
<212> TYPE: PRT
<213> ORGANISM: Artificial Sequence
<220> FEATURE:
<223> OTHER INFORMATION: Translated from Synthetic DNA

<400> SEQUENCE: 2

Met Met Ile Met Leu Glu Ala Val Tyr His Arg Met Gly Gln Asn Trp
1               5                   10                  15

Ser Tyr Ala Tyr Asn Asp Ser Thr Leu His Ile Arg Ile Arg Thr Lys
                20                  25                  30
```

-continued

Arg Asp Asn Val Pro Arg Ile Asp Leu His Cys Gly Glu Lys Tyr Asp
            35                  40                  45

Pro Glu Lys Tyr Lys Glu Thr Ile Pro Met Glu Arg Met Ala Ser Asp
    50                  55                  60

Gly Leu Phe Asp Tyr Trp Gln Ala Ala Val Gln Pro Arg Tyr Arg Arg
65                  70                  75                  80

Leu Val Tyr Tyr Phe Ala Leu His Ser Asp Asn Gly Asp Ala Val Tyr
                85                  90                  95

Phe Met Glu Lys Gly Phe Phe Asp Gln Pro Pro Lys Val Met Tyr Glu
                100                 105                 110

Gly Leu Phe Asp Phe Pro Tyr Leu Asn Arg Gln Asp Val His Thr Pro
            115                 120                 125

Pro Ala Trp Val Lys Glu Ala Ile Phe Tyr Gln Ile Phe Pro Glu Arg
            130                 135                 140

Phe Ala Asn Gly Asp Pro Ser Asn Asp Pro Glu Gly Val Gln Glu Trp
145                 150                 155                 160

Gly Gly Thr Pro Ser Ala Gly Asn Phe Phe Gly Gly Asp Leu Gln Gly
                165                 170                 175

Val Ile Asp His Leu Asp Tyr Leu Ser Asp Leu Gly Val Asn Ala Leu
            180                 185                 190

Tyr Phe Asn Pro Leu Phe Ala Ala Thr Thr Asn His Lys Tyr Asp Thr
            195                 200                 205

Ala Asp Tyr Met Lys Ile Asp Pro Gln Phe Gly Thr Asn Glu Lys Leu
            210                 215                 220

Lys Glu Leu Val Asp Ala Cys His Ala Arg Gly Met Arg Val Leu Leu
225                 230                 235                 240

Asp Ala Val Phe Asn His Cys Gly His Thr Phe Pro Pro Phe Val Asp
                245                 250                 255

Val Leu Asn Asn Gly Leu Asn Ser Arg Tyr Ala Asp Trp Phe His Val
                260                 265                 270

Arg Glu Trp Pro Leu Arg Val Asp Gly Ile Pro Thr Tyr Asp Thr
            275                 280                 285

Phe Ala Phe Glu Pro Ile Met Pro Lys Leu Asn Thr Gly Asn Glu Glu
            290                 295                 300

Val Lys Ala Tyr Leu Leu Asn Val Gly Arg Tyr Trp Leu Glu Glu Met
305                 310                 315                 320

Gly Leu Asp Gly Trp Arg Leu Asp Val Ala Asn Glu Val Asp His Gln
                325                 330                 335

Phe Trp Arg Glu Phe Arg Ser Glu Ile Lys Arg Ile Asn Pro Ser Ala
            340                 345                 350

Tyr Ile Leu Gly Glu Ile Met His Asp Ser Met Pro Trp Leu Gln Gly
            355                 360                 365

Asp Gln Phe Asp Ala Val Met Asn Tyr Pro Phe Thr Asn Ile Leu Leu
    370                 375                 380

Asn Phe Phe Ala Arg Arg Leu Thr Asn Ala Ala Glu Phe Ala Gln Ala
385                 390                 395                 400

Ile Gly Thr Gln Leu Ala Gly Tyr Pro Gln Gln Val Thr Glu Val Ser
                405                 410                 415

Phe Asn Leu Leu Gly Ser His Asp Thr Thr Arg Leu Leu Thr Leu Cys
            420                 425                 430

Ser Gly Asn Val Glu Arg Met Lys Leu Ala Thr Leu Phe Gln Leu Thr
            435                 440                 445

-continued

Tyr Gln Gly Thr Pro Cys Ile Tyr Tyr Gly Asp Glu Ile Gly Met Asp
    450                 455                 460

Gly Glu Tyr Asp Pro Leu Asn Arg Lys Cys Met Glu Trp Asp Lys Ser
465                 470                 475                 480

Lys Gln Asn Thr Glu Leu Leu Ala Phe Phe Arg Ser Met Ile Ser Leu
                485                 490                 495

Arg Lys Ala His Pro Ala Leu Arg Gly Ser Gly Leu Arg Phe Leu Pro
                500                 505                 510

Val Leu Glu His Pro Gln Leu Val Tyr Glu Arg Trp Asp Asp Asn
                515                 520                 525

Glu Arg Phe Leu Ile Met Leu Asn Asn Glu Asp Ala Pro Val Asn Val
530                 535                 540

Val Ile Pro Ala Ala Gln Pro Gly Ala Ser Trp Arg Thr Val Asn Gly
545                 550                 555                 560

Glu Pro Cys Ala Val Val Glu Glu Ser Ser Ile Gln Ala Ala Leu Pro
                565                 570                 575

Pro Tyr Gly Tyr Ala Ile Leu His Ala Pro Ile Ala Gly Thr Ala Glu
                580                 585                 590

<210> SEQ ID NO 3
<211> LENGTH: 776
<212> TYPE: PRT
<213> ORGANISM: Artificial Sequence
<220> FEATURE:
<223> OTHER INFORMATION: Translated from Synthetic DNA

<400> SEQUENCE: 3

Met Gly Arg Thr Pro Val Ser Thr Tyr Arg Leu Gln Ile Arg Lys Gly
1               5                   10                  15

Phe Thr Leu Phe Asp Ala Ala Lys Thr Val Pro Tyr Leu His Ser Leu
                20                  25                  30

Gly Val Asp Trp Val Tyr Leu Ser Pro Val Leu Thr Ala Glu Gln Gly
            35                  40                  45

Ser Asp His Gly Tyr Asp Val Thr Asp Pro Ser Ala Val Asp Pro Glu
    50                  55                  60

Arg Gly Gly Pro Glu Gly Leu Ala Ala Val Ser Lys Ala Ala Arg Ala
65                  70                  75                  80

Ala Gly Met Gly Val Leu Ile Asp Ile Val Pro Asn His Val Gly Val
                85                  90                  95

Ala Thr Pro Ala Gln Asn Pro Trp Trp Trp Ser Leu Leu Lys Glu Gly
                100                 105                 110

Arg Gln Ser Arg Tyr Ala Glu Ala Phe Asp Val Asp Trp Asp Leu Ala
            115                 120                 125

Gly Gly Arg Ile Arg Leu Pro Val Leu Gly Ser Asp Asp Leu Asp
130                 135                 140

Gln Leu Glu Ile Arg Asp Gly Glu Leu Arg Tyr Tyr Asp His Arg Phe
145                 150                 155                 160

Pro Leu Ala Glu Gly Thr Tyr Ala Glu Gly Asp Ala Pro Arg Asp Val
                165                 170                 175

His Ala Arg Gln His Tyr Glu Leu Ile Gly Trp Arg Arg Ala Asp Asn
                180                 185                 190

Glu Leu Asn Tyr Arg Arg Phe Phe Ala Val Asn Thr Leu Ala Gly Val
            195                 200                 205

Arg Val Glu Ile Pro Ala Val Phe Asp Glu Ala His Gln Glu Val Val
        210                 215                 220

-continued

Arg Trp Phe Arg Glu Asp Leu Ala Asp Gly Leu Arg Ile Asp His Pro
225                 230                 235                 240

Asp Gly Leu Ala Asp Pro Glu Gly Tyr Leu Lys Arg Leu Arg Glu Val
            245                 250                 255

Thr Gly Gly Ala Tyr Leu Leu Ile Glu Lys Ile Leu Glu Pro Gly Glu
        260                 265                 270

Gln Leu Pro Ala Ser Phe Glu Cys Glu Gly Thr Thr Gly Tyr Asp Ala
    275                 280                 285

Leu Ala Asp Val Asp Arg Val Leu Val Asp Pro Arg Gly Gln Glu Pro
290                 295                 300

Leu Asp Arg Leu Asp Ala Ser Leu Arg Gly Gly Glu Pro Ala Asp Tyr
305                 310                 315                 320

Gln Asp Met Ile Arg Gly Thr Lys Arg Ile Thr Asp Gly Ile Leu
            325                 330                 335

His Ser Glu Ile Leu Arg Leu Ala Arg Leu Val Pro Gly Asp Ala Asn
                340                 345                 350

Val Ser Ile Asp Ala Gly Ala Asp Ala Leu Ala Glu Ile Ile Ala Ala
            355                 360                 365

Phe Pro Val Tyr Arg Thr Tyr Leu Pro Glu Gly Ala Glu Val Leu Lys
    370                 375                 380

Glu Ala Cys Glu Leu Ala Ala Arg Arg Pro Glu Leu Asp Gln Ala
385                 390                 395                 400

Ile Gln Ala Leu Gln Pro Leu Leu Asp Thr Asp Leu Glu Leu Ala
                405                 410                 415

Arg Arg Phe Gln Gln Thr Ser Gly Met Val Met Ala Lys Gly Val Glu
            420                 425                 430

Asp Thr Ala Phe Phe Arg Tyr Asn Arg Leu Gly Thr Leu Thr Glu Val
            435                 440                 445

Gly Ala Asp Pro Thr Glu Phe Ala Val Glu Pro Asp Glu Phe His Ala
    450                 455                 460

Arg Leu Ala Arg Arg Gln Ala Glu Leu Pro Leu Ser Met Thr Thr Leu
465                 470                 475                 480

Ser Thr His Asp Thr Lys Arg Ser Glu Asp Thr Arg Ala Arg Ile Ser
                485                 490                 495

Val Ile Ser Glu Val Ala Gly Asp Trp Glu Lys Ala Leu Asn Arg Leu
            500                 505                 510

Arg Asp Leu Ala Pro Leu Pro Asp Gly Pro Leu Ser Ala Leu Leu Trp
            515                 520                 525

Gln Ala Ile Ala Gly Ala Trp Pro Ala Ser Arg Glu Arg Leu Gln Tyr
    530                 535                 540

Tyr Ala Leu Lys Ala Ala Arg Glu Ala Gly Asn Ser Thr Asn Trp Thr
545                 550                 555                 560

Asp Pro Ala Pro Ala Phe Glu Glu Lys Leu Lys Ala Ala Val Asp Ala
            565                 570                 575

Val Phe Asp Asn Pro Ala Val Gln Ala Glu Val Glu Ala Leu Val Glu
            580                 585                 590

Leu Leu Glu Pro Tyr Gly Ala Ser Asn Ser Leu Ala Ala Lys Leu Val
    595                 600                 605

Gln Leu Thr Met Pro Gly Val Pro Asp Val Tyr Gln Gly Thr Glu Phe
    610                 615                 620

Trp Asp Arg Ser Leu Thr Asp Pro Asp Asn Arg Arg Pro Phe Ser Phe
625                 630                 635                 640

Asp Asp Arg Arg Ala Ala Leu Glu Gln Leu Asp Ala Gly Asp Leu Pro
            645                 650                 655

Ala Ser Phe Thr Asp Glu Arg Thr Lys Leu Leu Val Thr Ser Arg Ala
        660                 665                 670

Leu Arg Leu Arg Arg Asp Arg Pro Glu Leu Phe Thr Gly Tyr Arg Pro
            675                 680                 685

Val Leu Ala Ser Gly Pro Ala Ala Gly His Leu Leu Ala Phe Asp Arg
        690                 695                 700

Gly Thr Ala Ala Ala Pro Gly Ala Leu Thr Leu Ala Thr Arg Leu Pro
705                 710                 715                 720

Tyr Gly Leu Glu Gln Ser Gly Gly Trp Arg Asp Thr Ala Val Glu Leu
                725                 730                 735

Asn Thr Ala Met Lys Asp Glu Leu Thr Gly Ala Gly Phe Gly Pro Gly
            740                 745                 750

Ala Val Lys Ile Ala Asp Ile Phe Arg Ser Phe Pro Val Ala Leu Leu
        755                 760                 765

Val Pro Gln Thr Gly Gly Glu Ser
    770                 775

<210> SEQ ID NO 4
<211> LENGTH: 2051
<212> TYPE: DNA
<213> ORGANISM: Artificial Sequence
<220> FEATURE:
<223> OTHER INFORMATION: Synthetic DNA

<400> SEQUENCE: 4
atgaaaagat ttatgaaact aacagccgta tggacactct ggttatccct cacgctgggc      60
cttttgagcc cggtccatgc agccccggat acctcggtat ccaacaagca gaatttcagc     120
acggatgtca tatatcagat cttcaccgac cggttctcgg acggcaatcc ggccaacaat     180
ccgaccggcg cggcatttga cggatcatgt acgaatcttc gcttatactg cggcggcgac     240
tggcaaggca tcatcaacaa aatcaacgac ggttatttga ccggcatggg cattacggcc     300
atctggattt cacagcctgt cgagaatatc tacagcgtga tcaactactc cggcgtccat     360
aatacggctt atcacggcta ctgggcgcgg gacttcaaga agaccaatcc ggcctacgga     420
acgatgcagg acttcaaaaa cctgatcgac accgcgcatg cgcataacat aaaagtcatc     480
atcgactttg caccgaacca tacatctccg gcttcttcgg atgatccttc ctttgcagag     540
aacggccgct tgtacgataa cggcaacctg ctcggcggat acaccaacga tacccaaaat     600
ctgttccacc attatggcgg cacggatttc tccaccattg agaacggcat ttataaaaac     660
ctgtacgatc tggctgacct gaatcataac aacagcagcg tcgatgtgta tctgaaggat     720
gccatcaaaa tgtggctcga cctcggggtt gacggcattc gcgtggacgc ggtcaagcat     780
atgccattcg gctggcagaa gagctttatg tccaccatta caactacaa gccggtcttc     840 accttcggcg aatggttcct tggcatcaat gagattagtc ggaatacca tcaattcgct     900 aacgagtccg ggatgagcct gctcgatttc gcctttgccc agaaggcccg gcaagtgttc     960
agggacaaca ccgacaatat gtacggcctg aaagcgatgc tggagggctc tgaagtagac    1020
tatgcccagg tgaatgacca ggtgaccttc atcgacaatc atgacatgga gcgtttccac    1080
accagcaatg cgacagacgg gaagctggag caggcgctgg cctttaccct gacttcacgc    1140
ggtgtgcctg ccatctatta cggcagcgag cagtatatgt ctggcgggaa tgatccggac    1200
aaccgtgctc ggattccttc cttctccacg acgacgaccg catatcaagt catccaaaag    1260

```
ctcgctccgc tccgcaaatc caacccggcc atcgcttacg gttccacaca ggagcgctgg   1320
atcaacaacg atgtgatcat ctatgaacgc aaattcggca ataacgtggc cgttgttgcc   1380
attaaccgca atatgaacac accggcttcg attaccggcc ttgtcacttc cctcccgcag   1440
ggcagctata acgatgtgct cggcggaatt ctaaacggca atacgttaac cgtgggtgct   1500
ggcggtgcag cttccaactt tactttggct cctggcggca ctgctgtatg cagtacaca   1560 accgatgcca cagctccgat catcggcaat gtcggcccga tgatggccaa gccaggggtc   1620
acgattacga ttgacggccg cggattcggc tccggcaagg aacggttta cttcggtaca   1680 acggcagtca ctggcgcgga catcgtagct tgggaagata cacaaatcca ggtgaaaatc   1740
cctgcggtcc ctggcggcat ctatgatatc agagttgcca acgcagccgg agcagccagc   1800
aacatctacg acaatttcga ggtgctgacc ggagaccagg tcaccgttcg gttcgtaatc   1860
aacaatgcca aacggcgct gggacagaat gtgttcctca cgggcaatgt cagcgagctg   1920
ggcaactggg atccgaacaa cgcgatcggc ccgatgtata atcaggtcgt ctaccaatac   1980
ccgacttggt attatgatgt cagcgttccg gcaggccaaa cgattgaatt taaattcctg   2040
aaaaagcata a                                                        2051

<210> SEQ ID NO 5
<211> LENGTH: 1775
<212> TYPE: DNA
<213> ORGANISM: Artificial Sequence
<220> FEATURE:
<223> OTHER INFORMATION: Synthetic DNA

<400> SEQUENCE: 5
atgatgatta tgctggaagc cgtttaccac cggatgggac aaaactggtc ctatgcctac     60
aatgattcga ccttgcatat ccgcatccgc accaagcggg acaatgtccc gcgcatcgac    120
ctgcactgcg gcgagaagta cgatccggag aagtacaagg aaaccattcc catggagcgt    180
atggcttctg acggactgtt tgattattgg caagccgccg tgcagcccag ataccgtaga    240
ttagtttatt acttcgcgct gcattccgac aacggcgatg ccgtttactt tatgagaag    300 ggattctttg atcagccgcc caaggtgatg tatgaaggat tgttcgactt cccttatctg    360
aatcggcagg atgtgcacac gcctccggca tgggttaagg aagcgatatt ctatcagatt    420
ttccccgagc gcttcgcgaa cggcgatccg tccaacgatc ccgaaggcgt gcaggaatgg    480
ggaggtacgc ccagcgccgg caatttcttc ggcgggatt tgcaaggcgt gatcgatcat    540
ctggactatc taagcgatct gggcgttaat gctttgtatt tcaaccccct attcgcggcc    600
accaccaacc ataaatacga tacggcggac tatatgaaga tcgaccccca attcggcacg    660
aacgaaaagc tcaaggagct ggtcgatgcc tgccatgccc ggggcatgcg cgtgctgctg    720
gacgccgtgt tcaaccactg cggccatacg tttccgccgt tcgtggacgt gttgaacaac    780
ggtctgaatt cgcgttacgc cggattggttc catgttcggg aatggcctct gcgggtcgtt    840
gacgggattc cgacctacga tacgttcgca ttcgaaccaa tcatgcccaa gctcaatacc    900
ggcaatgaag aagtgaaggc ttacctgttg aatgtcggcc gttactggct ggaggagatg    960
gggctggacg ctggcggct ggatgtcgcc aatgaggtgg accatcaatt ctggcgggaa   1020
ttccggagcg agatcaaacg gatcaatcct tcggcctata tcttaggcga gattatgcat   1080
gattccatgc cgtggctgca aggcgaccaa ttcgacgcgg tcatgaatta cccttcacg   1140 aacatcctgc tgaacttctt cgcccgcagg ctgacgaacg cggccgaatt cgcccaggcg   1200
```

| | |
|---|---:|
| atcggcacgc agctcgccgg ttatccgcag caggttacgg aagtgtcatt caatctgctc | 1260 |
| ggcagccatg acacgacgag gctattgacg ttgtgcagcg gcaatgtgga gcgcatgaag | 1320 |
| ctggcgacct tattccagct gacctatcag gggacgccat gcatctatta cggcgacgag | 1380 |
| atcggcatgg acggcgagta tgaccccctc aaccgcaagt gcatggaatg ggacaagagc | 1440 |
| aagcagaata cggagctgct tgcgttcttc cggagcatga tcagcctgcg caaggctcac | 1500 |
| cctgcgctgc gcgaagcgg actgcgcttc ctgccggtgc tggagcaccc gcagttgctg | 1560 |
| gtctatgagc gctgggacga taatgagcga ttcctcatca tgctgaataa tgaggatgct | 1620 |
| cccgtgaacg ttgttatccc ggcagctcag cccggcgctt cttggcgcac cgtgaacggc | 1680 |
| gagccatgcg cagtagtcga ggaaagttcg atacaggcgg ctctcccctcc ttacggttat | 1740 |
| gccatactgc atgcgcctat agcaggaacg gctga | 1775 |

<210> SEQ ID NO 6
<211> LENGTH: 2331
<212> TYPE: DNA
<213> ORGANISM: Artificial Sequence
<220> FEATURE:
<223> OTHER INFORMATION: Synthetic DNA

<400> SEQUENCE: 6

| | |
|---|---:|
| atgggcagaa cgccagtctc cacgtacagg ctgcagatca ggaagggatt cacactcttc | 60 |
| gacgcggcca aaaccgttcc gtacctgcac tcgctcggcg tcgactgggt ctacctttct | 120 |
| ccggtcctga ctgccgagca gggctccgac cacgggtacg acgtcaccga tccctccgcc | 180 |
| gtcgaccccg aacgcggcgg gccggagggc ctcgcggcgc tttccaaggc ggcccgcgcc | 240 |
| gcgggcatgg gcgtgctgat cgacatcgtg cccaaccacg tgggcgtcgc gacgccggcg | 300 |
| cagaacccct ggtggtggtc gctgctcaag gagggacgcc agtcccgtta cgcggaggcg | 360 |
| ttcgacgtcg attgggacct cgccggggga cgcatccggc tgccggtgct cggcagcgac | 420 |
| gatgacctcg accagctcga aatcaggggac ggggagctgc ggtactacga ccaccgattc | 480 |
| ccgctcgccg agggaaccta cgccgaaggc gacgccccgc gggatgtcca cgcccggcag | 540 |
| cactacgagc tcatcggctg gcgccgcgcg gacaacgagc tgaactaccg ccgcttttcc | 600 |
| gcggtgaaca cgctcgccgg cgtccgcgtg gaaatccccg ccgtcttcga cgaggcacac | 660 |
| caggaggtgg tgcgctggtt ccgcgaggac cttgcggacg gcctgcggat cgaccacccg | 720 |
| gacggcctcg ctgaccccga ggggtacctg aagcgactcc gggaagtcac cggcggcgct | 780 |
| tacctgctga tcgaaaagat cctggagccg ggggagcagc tgcccgccag cttcgagtgt | 840 |
| gaaggcacca caggctacga cgccctcgcc gacgtcgacc gggttctcgt ggaccgcgcg | 900 |
| ggccaggaac cgctggaccg gcttgacgcg tccctgcgtg gcggcgagcc cgccgactac | 960 |
| caggacatga tccgcggaac caagcgccgg atcaccgacg gtatcctgca ctcggagatc | 1020 |
| ctgcggctgg cccggctggt tccgggcgac gccaacgttt caatcgacgc cggagccgac | 1080 |
| gctctcgccg aaatcatcgc cgccttcccg gtctaccgca cctacctgcc ggagggcgcc | 1140 |
| gaggtcctga aggaggcgtg cgagcttgcc gcgcgtaggc ggccggaact cgaccaggcc | 1200 |
| atccaggctc tgcagccgct gctgctggac acggacctcg agcttgcccg gcgcttccag | 1260 |
| cagacctcgg gcatggtcat ggccaagggc gtggaggaca ccgcgttctt ccgctacaac | 1320 |
| cgcctgggca ccctcacgga agtgggcgcc gaccccaccg agttcgccgt ggagccggac | 1380 |
| gagttccacg cccggctggc acgcggcag gccgagcttc cgctgtccat gacgacgctg | 1440 |
| agcacgcacg acaccaagcg cagcgaggac acccgagcaa ggatttcggt catttccgag | 1500 |

```
gttgcgggtg actgggaaaa ggccttgaac cggctgcgcg acctggcccc gctgccggac    1560
ggcccgctgt ccgcgctgct ctggcaggcc attgccggcg cctggcccgc cagccgggaa    1620
cgcctgcagt actacgcgct gaaggccgcg cgtgaagcgg ggaactcgac caactggacc    1680
gatccggccc ccgcgttcga ggagaagctg aaggccgcgg tcgacgccgt gttcgacaat    1740
cccgccgtgc aggccgaggt ggaagccctc gtcgagctcc tggagccgta cggagcttcg    1800
aactccctcg ccgccaagct cgtgcagctg accatgcccg gcgtcccgga cgtctaccag    1860
ggcacggagt tctgggaccg gtcgctgacg gacccggaca accggcggcc gttcagcttc    1920
gacgaccgcc gcgccgcgct ggagcagctg gatgccggcg accttcccgc gtcatttacc    1980
gatgagcgga cgaagctgct agtgacgtcg cgcgcgctgc ggctgcgccg ggaccgtccg    2040
gagctgttca cggggtaccg gccggtcctg gccagcgggc ccgccgccgg gcacctgctc    2100
gcgttcgacc gcggcaccgc ggcggcgccg ggtgcattga ccctcgccac gcggcttccc    2160
tacgggctgg aacagtcggg tggatggcgg gacaccgccg tcgaacttaa caccgccatg    2220
aaagacgaac tgaccggtgc cggcttcgga ccggggcag tgaagatcgc cgacatcttc     2280
cggtcgttcc ccgttgcgct gctggtgccg cagacaggag gagagtcata a             2331
```